United States Patent [19]
Okajima et al.

[11] Patent Number: 5,821,402
[45] Date of Patent: Oct. 13, 1998

[54] THIN FILM DEPOSITION METHOD AND GAS SENSOR MADE BY THE METHOD

[75] Inventors: Yuichiro Okajima; Kei Kikuchi, both of Kawasaki; Takahiro Ide, Yokohama; Kenichi Nakamura, Tokyo, all of Japan

[73] Assignee: Tokyo Gas Co., Ltd., Tokyo, Japan

[21] Appl. No.: 812,557

[22] Filed: Mar. 7, 1997

[30] Foreign Application Priority Data

Mar. 11, 1996 [JP] Japan ................................. 8-052885
Oct. 3, 1996 [JP] Japan ................................. 8-263045

[51] Int. Cl.⁶ ........................... H01L 23/58; G01N 27/12
[52] U.S. Cl. ........................ 73/23.2; 73/31.06; 422/90; 422/98
[58] Field of Search ............................. 73/23.2, 31.06, 73/30.04; 422/98, 94

[56] References Cited

U.S. PATENT DOCUMENTS

| | | | |
|---|---|---|---|
| 3,831,432 | 8/1974 | Cox | 73/23 |
| 4,103,227 | 7/1978 | Zemel | 324/65 R |
| 4,198,851 | 4/1980 | Janata | 73/23 |
| 4,224,280 | 9/1980 | Takahama et al. | 422/98 |
| 4,387,165 | 6/1983 | Youngblood | 436/121 |
| 4,580,439 | 4/1986 | Manaka | 73/23 |
| 4,911,892 | 3/1990 | Grace et al. | 422/94 |
| 4,984,446 | 1/1991 | Yagawara et al. | 73/31.06 |
| 5,296,255 | 3/1994 | Gland et al. | 427/8 |
| 5,591,321 | 1/1997 | Pyke | 205/787 |
| 5,652,443 | 7/1997 | Kasai | 257/252 |

*Primary Examiner*—Hezron E. Williams
*Assistant Examiner*—J. David Wiggins
*Attorney, Agent, or Firm*—Armstrong, Westerman, Hattori, McLeland & Naughton

[57] ABSTRACT

A gas sensor including a substrate, a heater formed on said substrate, and a gas sensing material to be heated by said heater, wherein the area of the substrate under the heater is removed or reduced in its thickness to form a cavity. The thickness of the layer of the gas sensing material is reduced gradually toward the peripheral of the gas sensing material.

10 Claims, 6 Drawing Sheets

THIN FILM DEPOSITION METHOD AND GAS SENSOR MADE BY THE METHOD

TECHNICAL FIELD OF THE INVENTION

The present invention relates to a thin film deposition method for forming a thin film on a predetermined position from a preferred material and more particularly to a thin film deposition method for forming a thin film on a predetermined position from a preferred material by use of the heat from a heater which is equipped on a member to perform a function of said member, and a gas sensor made by the method.

BACKGROUND OF THE INVENTION

Methods for depositing thin film on a predetermined position from a preferred material are utilized in various technical fields. For example, in a gas detecting element, a layer of tin oxide is formed on the surface of the element as a sensing material.

In a gas detecting element utilizing tin oxide sensing material, the element detects gas from a change of resistance of the sensing material. Therefore, the tin oxide film is formed between the lead wires for detecting resistance, and at the same time a heater for heating the tin oxide to an operating temperature for detecting gas is placed close to the tin oxide layer.

The prior art method of manufacturing a thin layer gas detecting element is as follows. In a metal mask method, electrodes for the tin oxide are formed on a substrate comprising a heater. A metal mask having a preferred opening is placed above said substrate, and a tin oxide film is deposited through the opening on a preferred area. Also known is the etching method wherein the sensing material film is deposited on the surface of a substrate comprising a heater, then unnecessary part of the film is removed by etching.

At present, a gas sensor for sensing gas leak is utilized for detecting the leak of city gas and LP gas. There are mainly two types of gas sensors, the semiconductor type and the resistance methanometer type, many of which are manufactured by a method of sintering an oxidation medium material or semiconductor around a heater wire made of Pt, Pd and the like. However, by this method, there is a limit to the miniaturization of the sensor. Further, the power consumption was somewhat large, limiting long hours of use by battery.

A thin film-type gas sensor formed by utilizing semiconductor fine process technique is also known. This type of semiconductor thin film gas sensor comprises of a substrate, an insulating layer, a heater, a protective layer, an electrode and semiconductor body formed in layers, and the portion of the substrate under the heater is etched and removed to provide thermal insulation from the substrate. In many cases the substrate is a single crystalline substrate of silicon, sapphire and the like for etching, and the insulating layer and the protective layer are $SiO_2$ layers, $Si_3N_4$ layers or the combination of the two for high insulation and heat resistance characteristics. As for the heater, stable material such as Pt, W, polycrystalline and the like are utilized. The electrode is formed of Pt and the like, and the semiconductor body is formed by metal oxide such as $SnO_2$, ZnO, NiO, CuO and the like.

Such gas sensors could be designed in very small sizes with very low power consumption, and with a high speed of temperature rise. Therefore, the gas leak could be sensed even by intermittent heating of the heater, and the power consumption of the heater could further be lowered.

SUMMARY OF THE INVENTION

However, in the metal mask method, it is difficult to deposit the sensing material with sufficient accuracy, because the size of the mask is thick and the positioning of the metal mask is very difficult. Therefore, the metal mask method can not be applied to detecting elements formed in small sizes on a silicon substrate.

On the other hand, by using the etching method, the manufacturing of detecting elements needs the following troublesome steps. A deposition step of forming a thin film of tin oxide on the upper surface of the detecting electrode, a step of applying resist on the tin oxide thin film, a step of curing the resist to a preferred shape by ultraviolet irradiation, a step of removing the unnecessary part of the tin oxide layer by etching gas or etching solution, and a step of removing the resist layer.

Further, when soaked in etching solution, a part of the necessary tin oxide layer can be eroded by the solution on the side surface of the tin oxide layer. In the step of removing the resist, a remover such as boiling sulfuric acid is utilized, which effects the surface structure or the status of the tin oxide layer, and thus changes of the gas sensitivity. The gas sensitivity changes of tin oxide when its surface is effected by strong acid such as $SO_4^{2-}$ is reported in A. Keshavaraja et al., "Sensors and Actuators B", 23, P75–81 (1995).

The present invention utilizes the heater equipped in the member to heat the preferred material close to the heater to a film deposition temperature, and to form a thin film by said material.

The equipped heater is utilized to heat the preferred position, and the material to be deposited is made to contact to the heated portion in a gas or a mist form. Then, a thermal process (thermal decomposition) of the material proceeds only in the area heated by the heater, and a thin film of the material is formed on such area. The deposited material is heated by a heater when used as a sensor and the like, so the thin film should be formed in such area where the heat from the heater is transmitted, and no where else. It is even not preferable to deposit the layer other than such area, so the method is highly efficient in forming a thin film with a preferred material.

A thermal chemical vapor deposition (CVD) system or a spray thermal decomposition process system can be used as the deposition method of a material. These methods heat the surface temperature of the preferred area, and form a thin film from a preferred material by a thermal process. It is preferable to use a heater equipped to the product or member to perform a part of its function, but not limited to such. The heater can be used to heat a material to form a thin film, and removed after the step. Further, it can be an element equipped not as a heater but which can be heated some how, for example with current.

The position to deposit the material is not limited to the area directly above the heater, but also to the side of the heater, or below the heater. Further, the heater can be positioned so as to directly heat the material, or to have an insulating layer or the like inbetween. The form of the film is not limited to thin film. It can be in a spot form, or it can be in any preferred shape by using a heater having different shapes or by utilizing a heat shielding material.

Further, when a plurality of elements is formed on one silicon substrate so as to cut them apart after they are formed, each heater mounted on each element should be wired so that it can be heated at the same time. By doing so, the connection of the power to the heater can be simplified, and the preferred material can be deposited easily by heating all the heater on one silicon substrate at the same time. The wiring connecting each heater can be a series connection, but preferably a parallel connection so as to minimize the effect of wire disconnection.

The gas sensors explained in the background of the invention are formed by layering a thin film of various materials. Each of these materials has different thermal expansion characters, which make the sensor weak to temperature change and lower the durability of the sensor. Especially when the heater is heated intermittently, the temperature change is very large in each portion, and by repeated heating, the sensor easily breaks.

For example, when heating the heater up to 550° C. by heating it intermittently every 0.1 seconds, the gas sensor breaks by heating it for a few hundred thousand times. The sensor needs to survive at least five million times of intermittent heating in order to use the sensor for city gas and LP gas leak detector. Therefore, the above gas sensor has problems for practical use.

The present invention is aimed at solving the above problem by providing a gas sensor having a sufficient durability to intermittent heating of the heater, and therefore can be used for a long period of time. The present invention is related to a gas sensor having the structure explained hereinafter to solve the above mentioned problem.

The present gas sensor comprises on a substrate a heater and a gas sensing material being heated by the heater wherein the substrate under the heater is etched and removed or reduced of its thickness to form a cavity thereto, and the thickness of the layer of gas sensing material is reduced gradually toward the peripheral of said gas sensing material.

Further, the present gas sensor is formed so that the internal stress of the gas sensing material will minimize when heated to a gas sensing temperature.

Still further, the thickness of the gas sensing material is formed so as to correspond to the temperature distribution of the gas sensing material when being heated by the heater.

Further, the gas sensing material is a semiconductor layer.

Further, the substrate of the present gas sensor is formed of silicon, having an insulating layer formed between the silicon substrate and the heater, a protective layer covering at least the upper surface of the heater, a semiconductor layer over the protective layer, and an electrode for detecting the electric resistance of the semiconductor layer, wherein the gas is sensed from the change of electric resistance of the semiconductor layer.

In the present invention, the insulating layer and the protective layer is a $SiO_2$ layer or a composite layer of $SiO_2$ and $Si_3N_4$, the heater is a polycrystalline silicon, the semiconductor layer is $SnO_2$ and the electrode is Pt.

Further, a projecting portion protruding from said substrate is formed, wherein said heater, said semiconductor layer and said electrode is formed on said projecting portion. The projecting portion either a bridge structure or a cantilever structure.

Still further, a catalyst for encouraging a predetermined reaction of the gas can be used instead of said gas sensing material.

The method to form the thickness of the layer of gas sensing material so as to reduce gradually toward the peripheral of said gas sensing material is realized by heating the heater formed on the substrate to deposit a semiconductor material on the substrate by a thermal chemical vapor deposition (CVD) method and the like. According to the thermal CVD method, the semiconductor layer is deposited on the surface of the substrate and the like in a speed corresponding to the temperature, resulting in a semiconductor layer having a thickness corresponding to the temperature distribution of the gas sensing material, having a center in the center area of the heater and changing gradually. Thus, the thickness of the semiconductor layer reduces gradually toward the peripheral of the semiconductor layer.

Further, at the time of the deposition of the semiconductor material, the substrate, the electrode and other members of the sensor are heated to a temperature close to the actual gas sensing condition. Therefore, by depositing the semiconductor layer in such condition, no internal stress occurs at the time of use, or when being heated.

By the description that the thickness of the layer reducing gradually, it means that when the angle of the outline of the thickness changing area and the deposited portion of the layer is the tilt angle, the thickness of the layer reduces in a smaller average tilt angle than the average tilt angle of the semiconductor layer formed by an ordinary etching method.

The semiconductor layer formed by the present method will effectively absorb the stress occurring from the difference in thermal expansion rate of each material at the time of heating. Therefore, a deformation stress will not be concentrated on a certain portion, and the durability of the gas sensor will increase greatly.

DETAILED DESCRIPTION OF THE INVENTION

The thin film deposition method of the present invention will now be explained using the example of a thin film gas sensor wherein a film of tin oxide is deposited near the heater.

Figure 1:
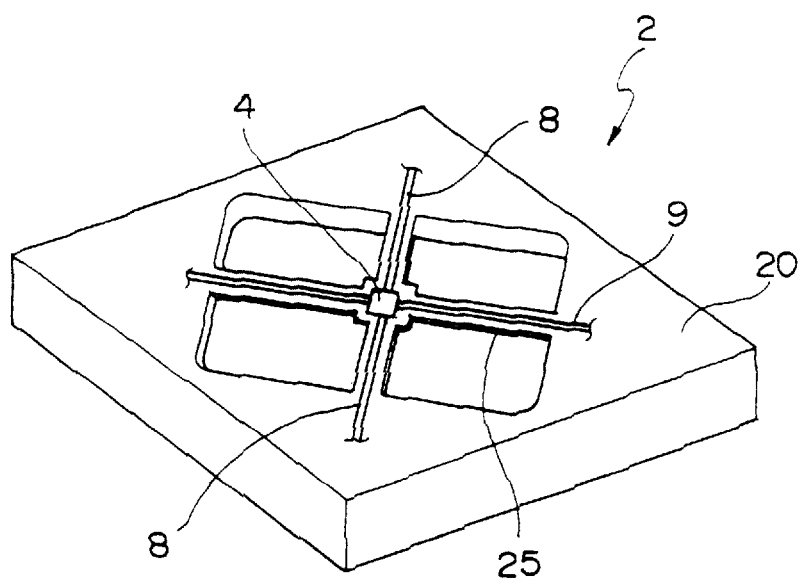
FIG. 1 is a schematic view of the gas sensor utilizing the thin film deposition method of the present invention.
Figure 2:
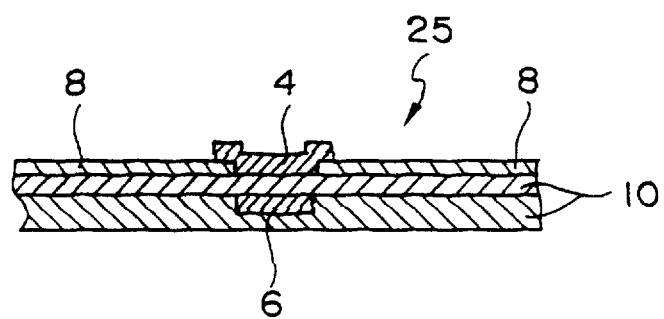
FIG. 2 is a partial cross-sectional view of the gas sensor of FIG. 1.

FIG. 1 shows an example of a gas sensor. The sensor 2 of FIG. 1 comprises a crossing beam 25 on a silicon substrate 20. A tin oxide 4 is positioned on the crossing point of the beam 25. FIG. 2 is a cross-sectional view of the beam 25. As is shown in FIG. 2, on the surface of the beam 25 is formed a tin oxide 4, underneath which is a heater 6 placed via an insulating layer 10. The heater 6 is heated with current through the lead wire 9 (FIG. 1), heats the tin oxide 4 placed on the surface. The sensor detects gas by measuring the change of electric resistance of the tin oxide 4 through an electrode 8.

The method of manufacturing the sensor 2 includes a step of forming the heater 6 on the upper surface of the silicon substrate 20 via an insulating layer 10, and then forms the crossing beam structure by the beam 25. The beam structure and the heater 6 are formed by a prior art method. For example, the heater 6 can be formed by utilizing a metal having large electric resistance characters, or by changing the width of the metal partially. Then an insulating layer 10 is formed above the heater 6, and an electrode 8 for detecting gas is placed on the insulating layer 10. Then, a cross-shaped resist layer is formed on the silicon substrate 20, and the surface layer is formed in a cross shape. Further, the substrate under the heater is etched and removed in order to form a beam structure. However, the beam structure is not indispensable, and the sensor 2 can be formed on a diaphragm.

Figure 3:
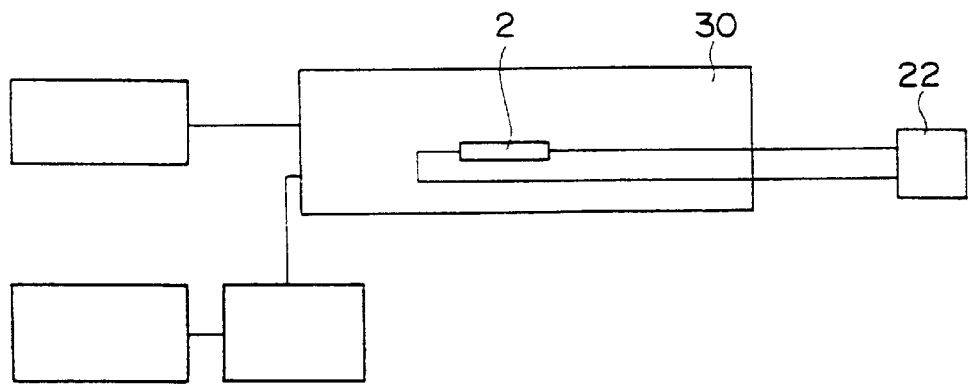
FIG. 3 shows the reactor.

After the above steps are completed, the silicon substrate 20 is positioned inside a reactor 30 as is shown in FIG. 3. Then the heater 6 is heated with current through an electrode 22 via a lead wire 9, and a material gas of the tin oxide 4, for example, tetramethyltin or tin chloride, is supplied to the reactor 30 by a carrier gas, for example, nitrogen, argon, helium, with an oxidizing agent like oxygen, ozone, nitrogen-oxide and water vapor.

The current through to the heater 6 is controlled so as to only heat the insulating layer 10 directly above the heater 6 to a temperature to start the thermal decomposition of the material gas. The material gas is supplied by blowing the carrier gas into the tetramethyltin and the like, and sending gas which passed through the solution into the reactor 30.

When the surface of the heater 6 is heated up to the thermal decomposition temperature of the material gas, the thermal decomposition of the material gas proceeds at the heated area, and the tin oxide 4 layer is formed. By the present method, tin oxide 4 is deposited directly above the heater 6 without undesired deposition in other areas.

Therefore, by the present method, the tin oxide 4 film deposition to the area close to the heater 6 on the sensor 2 is simplified, cost effective and time saving. Further, it has no effect to the sensing characteristics of the tin oxide film since no etching solution is used in the process, manufacturing a sensing element having a desired performance.

The preferred embodiment of the thin film deposition method of the present invention will now be explained.

In the present embodiment, a thin film gas sensor utilizing tin oxide as sensing material was manufactured. First, a heater and an electrode for the tin oxide was formed on the substrate. The heater and the electrode are formed by known methods, wherein the heater layer is deposited on the substrate via an insulating layer by a sputtering method, and then the layer is etched to form a heater wire. Then a silicon dioxide layer is formed on it as an insulating layer, and then two thin-layer platinum electrodes are formed opposing each other. The method here is no different from the prior art method.

After forming the heater and the electrode on the substrate, the heater is connected to the power supply, and the substrate is placed inside the reactor. The reactor is not heated so as to keep the inside temperature to room temperature. Then, the material gas (tetramethyltin) is supplied to the reactor using argon gas as the carrier gas and oxygen as oxidizing agent. And the surface of the substrate is heated by the heater. The pressure inside the reactor is 3 Torr, the voltage impressed to the heater is 3 V, and the temperature of the surface heated by the heater is 600° C. This condition is maintained for 20 minutes to form the thin film.

Figure 4:
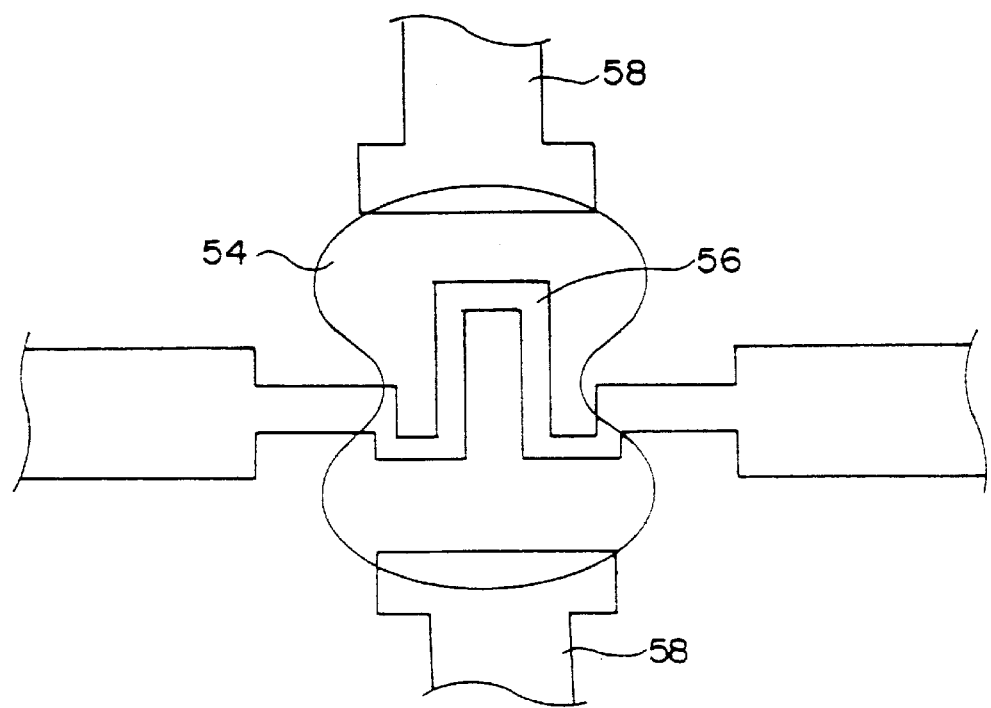
FIG. 4 shows the deposited thin film of the thin film deposition method of the present invention.

FIG. 4 shows the result gained by measuring the thickness of the film after the substrate is removed from the reactor. The contour line showing the film thickness of 180 nm is shown as tin oxide 54 in FIG. 4. As shown in FIG. 4, the tin oxide 54 is selectively deposited only in the area directly above the heater 56, which is between the detecting electrode wires 58. It is confirmed that the area directly above the heater 56 is heated up to a sufficient temperature, and that said heat deposits the tin oxide 54 reliably.

Figure 5:
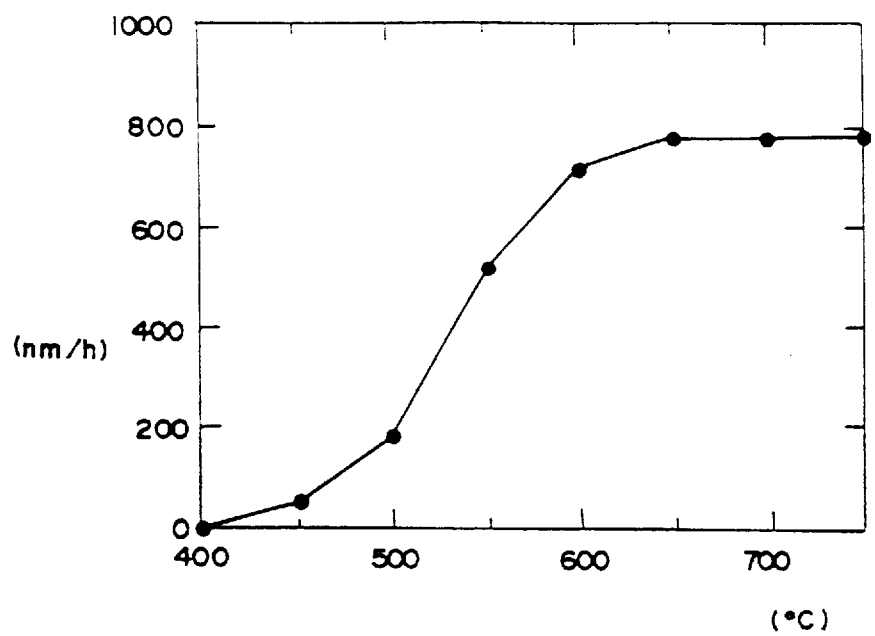
FIG. 5 is a graph showing the relation between the temperature of the substrate and the deposition rate of the tin oxide.

FIG. 5 shows the result of the experiment on the relation between the temperature of the substrate and the deposition rate of the tin oxide. As shown in FIG. 5, the deposition rate rises greatly from the surface temperature of about 450° C. This rapid increase of the deposition rate indicates that when the substrate temperature is kept in a range of about 600° C. to 650° C., the deposition of the tin oxide is rapid, and the thickness of the tin oxide film gained is uniform, but on the other hand, in the area not very close to the heater where the surface temperature rises to only about 400° C., nearly no deposition occurs. Therefore, the deposition area of tin oxide could be limited to the desired area.

The thin film deposition method of the present invention wherein the equipped heater heats the desired area to deposit the desired material has the following effects.

The desired area can be heated easily without the use of a special heating device such as an electric furnace, so the cost needed to heat the substrate is very low.

The deposition of the desired material is limited to the desired area because only the necessary area is heated. The other unnecessary areas will not be heated, so no deposition occurs in unwanted areas.

There is no need for etching processes to remove materials, so the manufactured device shows desired characteristics.

The embodiment of the gas sensor of the present invention will now be explained.

Figure 6:
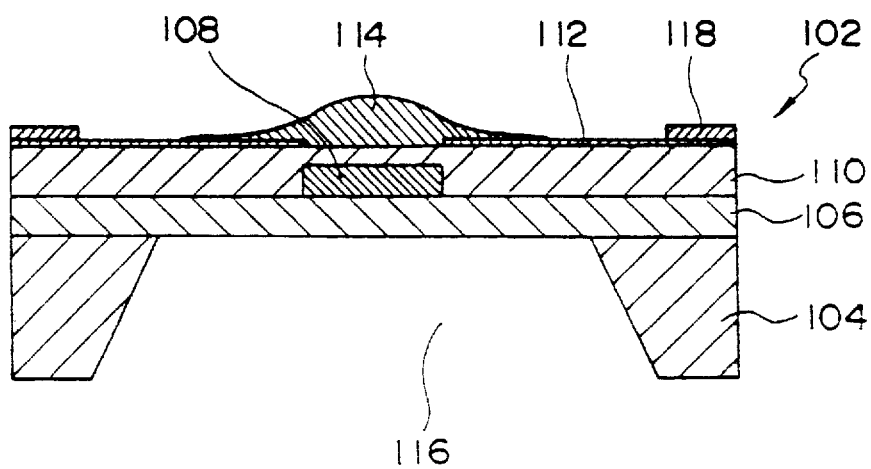
FIG. 6 is a cross-sectional view of the gas sensor of the present invention.

The gas sensor 102 is shown in FIG. 6. As is shown in FIG. 6, the gas sensor 102 comprises of a substrate 104, an insulating layer 106 on the substrate, a heater 108 on the insulating layer 106, a protective layer 10, an electrode 112 and a semiconductor 114 which is the gas sensing material. The substrate 104 is partly removed under the insulating layer 106 to form a cavity 116.

The substrate 104 is silicon, and the insulating layer 106 is formed of $SiO_2$. The heater 108 is formed of polycrystalline silicon, and on the heater 108 is a protective layer 110 made of the same material as the insulating layer 106. On the protective layer 110 is a pair of electrodes 112, and the semiconductor for sensing gas formed of $SnO_2$ is formed so as to cover a part of the heater 108. The cross section of the semiconductor is mountain-shaped, the peripheral of which is gradually reduced of its thickness toward the edge and being connected to the protective layer 110.

The semiconductor 114 will now be explained in detail.

The semiconductor 114 is formed so that the thickest portion is above the center of the heater 108, and the thickness decreases gradually toward its peripheral. Further, the semiconductor 114 is formed so that the internal tension stress or the pressure stress will be minimized when heated to a predetermined temperature by the heater 108. That is, when the semiconductor 114 is heated to a gas sensing condition by charging the heater 108, the substrate 104, the insulating layer 106, the heater 108 and the like will be deformed by thermal expansion and the like, and the deforming stress will be added to the semiconductor 114. The semiconductor 114 itself will be deformed by temperature rise. The semiconductor 114 is formed so that the internal stress is minimized at the driving temperature of the gas sensor 102 in spite of such thermal deformation.

The thickness of the semiconductor 114 is formed so as to correspond to the temperature distribution on the substrate 104, or to be more precise, on the protective layer 110. Therefore, the stress caused by the difference in thermal expansion rate of each material is effectively absorbed so that deformation stress by the change of temperature will not concentrate in one portion, which results in longer use of the gas sensor even when heated intermittently.

Further, the stress on the semiconductor 114 is minimized when the sensor 102 is in use by heating the semiconductor 114, deformation caused by temperature rise is not likely to happen. A high performance and high durability will be realized by the sensor 102 with minimized danger of damage.

Next, an embodiment of the method of manufacturing the gas sensor 102 of the present invention will be explained.

First, an insulating layer 106 is deposited on a single crystal substrate 104 of silicon and the like. The insulating layer 106 can be formed of $SiO_2$, $Si_3N_4$, $Al_2O_3$, MgO or a composition of such materials. When the substrate is of a material having insulating characteristics such as sapphire, this insulating layer 106 is not necessary. Next, a heater 108 is formed above the insulating layer 106. The heater 108 can be polycrystalline silicon, Pt, W and the like. Then, a protective layer 110 is formed to cover the whole surface of the substrate including the heater 108. The protective layer can be formed of but not limited to $SiO_2$ as is with the insulating layer.

When an electrode 112 of Pt and the like is formed on top of the protective layer, a heater 108 and an electrode 118 for taking out the signal of electrode 112 is formed by Au and the like. Then, anisotropy etching is performed from the back surface of substrate 104 to form a cavity 116 on the portion under the heater 108. The anisotropy etching can also be performed from the front surface of substrate 104, and in this case, a bridge structure or a cantilever structure is formed on the substrate 104. The method until this step is the same as the method of manufacturing a heat wire-type micro heater formed by a micro machining process technique.

Next, a gas sensing material, which is the semiconductor 114, is deposited using a thermal CVD method and the like by heating the heater. In detail, the heater 108 formed on the substrate 104 is heated with current to the material such as organic metal to a temperature above the thermal decomposition temperature of the material, and the vapor of the material is mixed with oxidizing agent such as oxygen and ozone so as to contact the heater 108. Then, by thermal decomposition, a layer of $SnO_2$ is formed near the heater 108. The deposition of $SnO_2$ starts when it reaches a predetermined temperature, and the rate of deposition will rise with the temperature rise. By this reason, the thickness of the layer will maximize in the area directly above the heater 108 and will decrease gradually in the area away from the heater 108. The thickness of the layer will be nearly zero at the portion where the temperature will be the initiation temperature of the thermal decomposition. Therefore, the thickness of the layer will gradually decrease toward the peripheral of the semiconductor 114.

Further, the semiconductor material to be deposited is not limited to $SnO_2$ but the metal oxide such as ZnO, NiO, CuO and the like can be used, and the material to be supplied should be selected by the material to be deposited. Further, the depositing method is not limited to thermal CVD method, but also a mist thermal decomposition method could be utilized. In the latter method, the material is processed in mist form instead of vapor, and deposited in the same way as the thermal CVD method. When the temperature of heater 108 is set higher than the initiation temperature of the thermal decomposition of the material, the semiconductor can be deposited in a wide area. In contrast, when only the area close to the heater 108 should be deposited, the temperature of the heater 108 should be only a little higher than the initiation temperature of the thermal decomposition of the material.

In the case of the bridge structure of the cantilever structure, the semiconductor layer will be deposited all around the heater 108, but this will not cause problems since the cross section of the semiconductor layer deposits in each surface is gently mountain-shaped.

Figure 7:
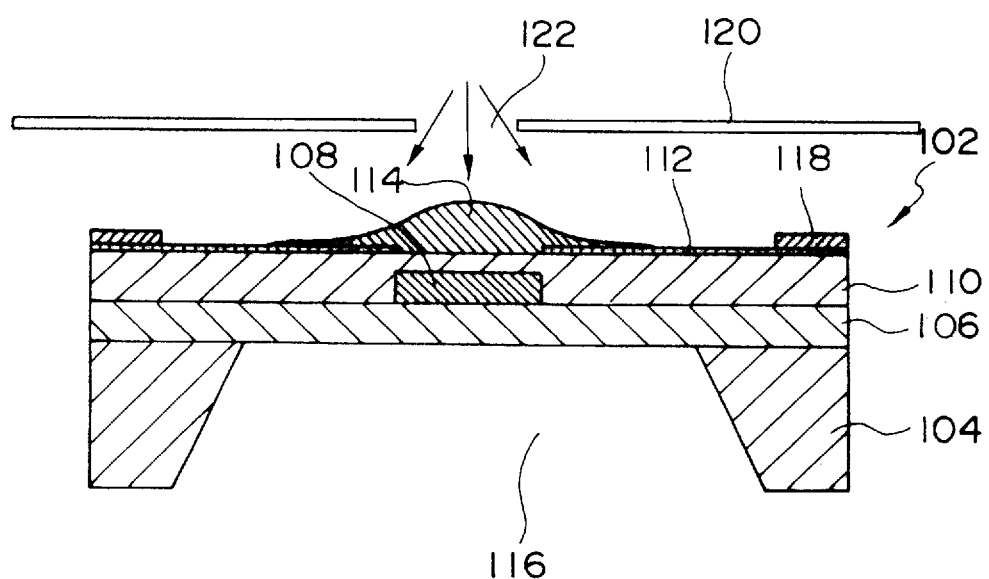
FIG. 7 is a cross-sectional view of the manufacturing method of the gas sensor of the present invention.

A sputtering method or a vaporizing method can also be utilized for the deposition of semiconductor 114. In this case, as is shown in FIG. 7, a metal mask 120 is placed so that the hole 122 formed on the metal mask 120 is placed directly above the heater 108 having a predetermined distance between the substrate 104. Then, sputtering and the like is performed through the hole 122. Then, a semiconductor 114 having a mountain-shape cross section with the maximum thickness positioned directly above the center of the heater 108 is deposited on the substrate by the particles passing through the hole 122. The deposition area can be controlled by the distance between the metal mask 120 and the substrate 104, or the diameter of the hole 122. Further, it is not necessary to heat the heater 108 in this method, but it can be heated to a driving temperature of the gas sensor 102 regarding the internal stress and the like.

As is explained above, the gas sensor 102 of the present embodiment is formed so that the layer thickness of the semiconductor 114 for detecting gas decreases toward its peripheral, resulting in effective absorption of stress occurring by the difference in the thermal expansion rate of each material at the time of heating, resulting in great increase of durability.

Further, at the time of deposition of the semiconductor 114, the substrate 104 and other members are also heated, and the semiconductor 114 is deposited at such temperature condition. Therefore, there is no great deformation stress to the semiconductor when heated, and the internal stress is minimized, resulting in increasing durability. In contrast, under normal temperature which is lower than the driving temperature, the gas sensor 102 or at least the semiconductor 114 will be in a compressed state when considering the fact that many material will expand by temperature rise. Therefore, the semiconductor is stable in both heated and normal conditions.

The preferred embodiment of the gas sensor of the present invention will now be explained.

In the present embodiment, a silicon single crystal substrate is used as the substrate, and on the substrate, a $SiO_2$ layer is deposited as an insulating layer. Further, a heater is formed on the insulating layer by a polycrystalline silicon comprising P ion as impurity. Next a layer of $SiO_2$ is deposited on the whole surface of the substrate including the heater as a protective layer, and an electrode for measuring the electric resistance of the semiconductor so as to detect gas is formed on the protective layer by Pt. Then, a cavity is formed below the insulating layer by anisotropy etching of the substrate from underneath.

The semiconductor which works as the gas sensor is $SnO_2$, and it is deposited by a thermal CVD method. Deposition is done by forming the heater and the electrodes on the substrate as is explained, and then connecting a power line to the heater and then placing the substrate inside a reactor. The semiconductor is made from tetramethyltin, and the vapor of tetramethyltin is supplied to the reactor using argon gas as the carrier together with oxygen as the oxidizing agent. During this, the temperature inside the reactor is kept to 70° C., and the pressure is controlled to 3 Torr. Further, by the current through the heater, the temperature of the heater is controlled to be 550° C. The deposition of $SnO_2$ is done for one hour.

Figure 8:
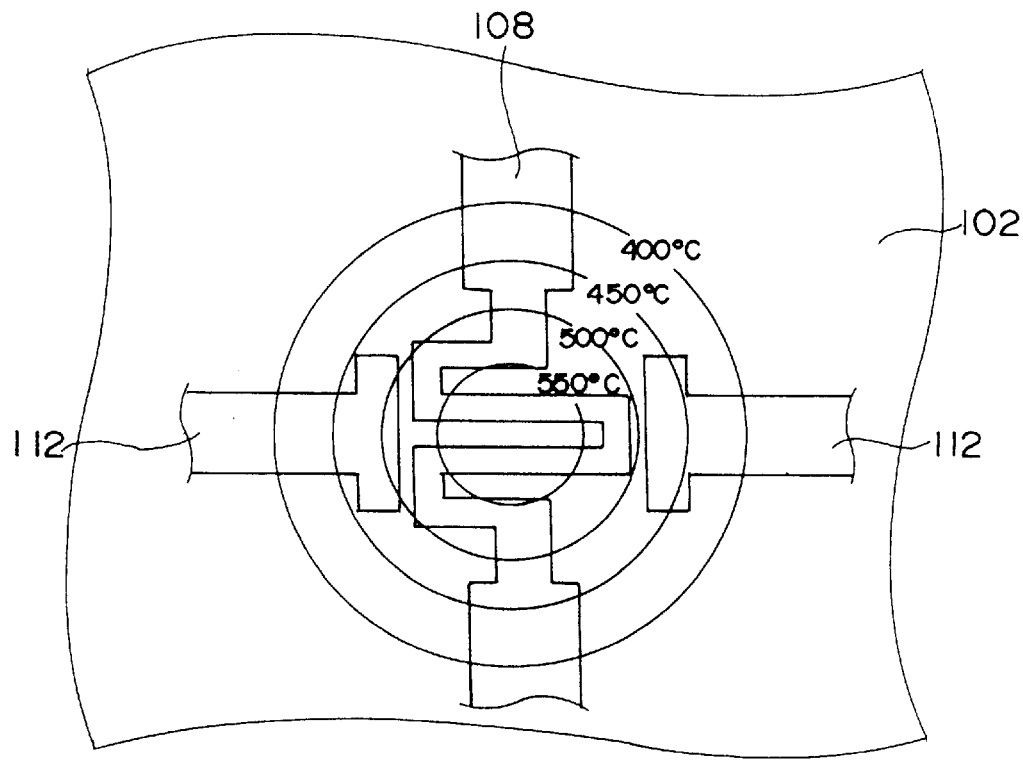
FIG. 8 is a temperature distribution of the gas sensor.
Figure 9:
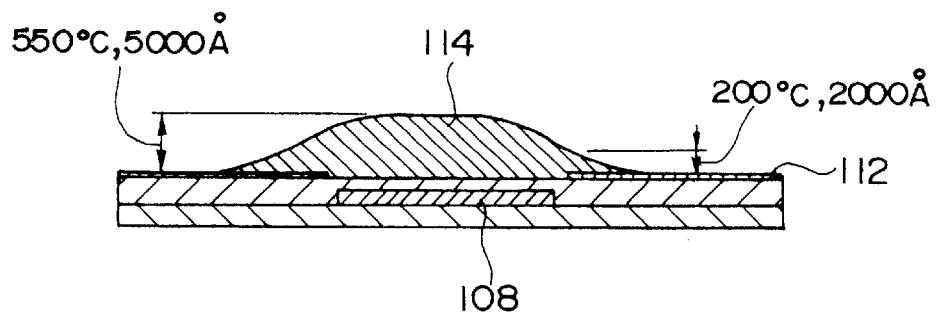
FIG. 9 shows the thickness of the formed layer.
Figure 10:
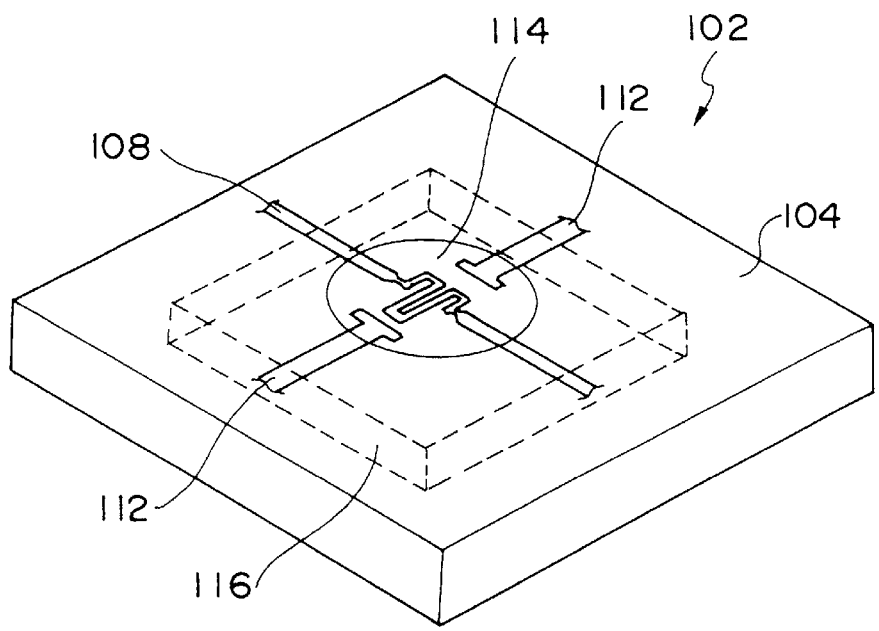
FIG. 10 is a schematic view of the gas sensor of the present invention.

FIG. 8 shows the temperature distribution of the sensor when the temperature of the center of the heater is 550° C. FIG. 5 shows the deposition rate of the $SnO_2$. From the relation of the two, the thickness of the layer of $SnO_2$ turns out to be as shown in FIG. 9 wherein the thickness of the layer decreases toward the peripheral of the layer. The same thing is determined by an observation of optical interference.

Figure 11:
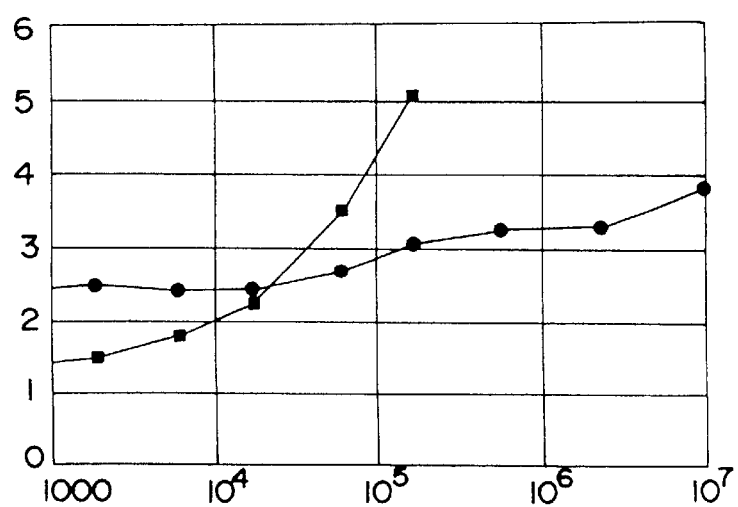
FIG. 11 shows the experiment result of the durability test.

Next, a durability test of the gas sensor 102 of the present embodiment and a gas sensor of the prior art is performed. The test is done by heating the heater 108 intermittently to 550° C. every 0.1 second, and measured the resistance of $SnO_2$. The result is shown in FIG. 11. As is apparent from FIG. 11, the sensor manufactured by the prior art technique has its $SnO_2$ layer break after only a hundred and few thousand times of heating, but in contrast, there is no break of $SnO_2$ layer examined after ten million times of heating of the present sensor. By this test result, the sensor of the present invention can be said to have ten times to more than hundred times better durability than the sensor of the prior art.

Further, in the present embodiment, the peripheral of the semiconductor 114 on the heater 108 is formed to have a gradually decreasing layer thickness. However, the supporting structure of the semiconductor 114 such as the protective layer 110 can be formed to have such structure. By doing so, not only the semiconductor 114 but also the structure itself of the sensor becomes highly durable to the temperature change caused by the heating.

By the structure of the present invention, a sensor with high durability can be gained.

What is claimed is:

1. A gas sensor comprising:

a substrate;

a heater formed on said substrate; and a gas sensing material to be heated by said heater, as disposed over said heater and substrate; wherein the area of the substrate under said heater is removed or reduced of its thickness to form a cavity thereto;

characterized in that the thickness of the layer of said gas sensing material is reduced gradually toward the peripheral of said gas sensing material, thereby providing a longer lifetime gas sensor having high durability against heating at operating temperature.

2. The gas sensor of claim 1 wherein the internal stress of said gas sensing material is minimized when said gas sensing material is heated to a gas sensing temperature by said heater.

3. The gas sensor of claims 1 or 2 wherein the thickness of said gas sensing material is formed so as to correspond to the temperature distribution of the gas sensing material when being heated by the heater.

4. The gas sensor of claim 1 wherein said gas sensing material is a semiconductor layer.

5. The gas sensor of claim 4 wherein said substrate is formed of silicon, further comprising:

an insulating layer formed between said silicon substrate and said heater;

a protective layer covering at least the upper surface of the heater;

a semiconductor layer formed over the protective layer; and an electrode for detecting the electric resistance of said semiconductor layer;

wherein the gas is sensed from the change of electric resistance of said semiconductor layer.

6. The gas sensor of claim 5 wherein said insulating layer and said protective layer is a $SiO_2$ layer or a composite layer of $SiO_2$ and $Si_3N_4$, said heater is a polycrystalline silicon, said semiconductor layer is $SnO_2$ and said electrode is Pt.

7. The gas sensor of claim 4, 5 or 6 wherein said area of the substrate which is removed or reduced of its thickness to form a cavity thereto is formed on a projecting portion protruding from said substrate, wherein said heater, said semiconductor layer and said electrode is formed on said projecting portion.

8. The gas sensor of claim 7 wherein said projecting portion is a bridge structure.

9. The gas sensor of claim 7 wherein said projecting portion is a cantilever structure.

10. The gas sensor of claim 1 or 2 wherein a catalyst for encouraging a predetermined reaction of the gas is used instead of said gas sensing material.

* * * * *